United States Patent [19]

Wittkampf

[11] 4,142,530
[45] Mar. 6, 1979

[54] EPICARDIAL LEAD

[75] Inventor: Frederik H. M. Wittkampf, Brumen, Netherlands

[73] Assignee: Vitatron Medical B. V., Dieren, Netherlands

[21] Appl. No.: 883,455

[22] Filed: Mar. 6, 1978

[51] Int. Cl.² ............................................. A61N 1/04
[52] U.S. Cl. ................................. 128/418; 128/419 P
[58] Field of Search ............................ 128/418, 419 P

[56] References Cited

U.S. PATENT DOCUMENTS

| 3,754,555 | 8/1973 | Schmitt | 128/418 |
| 3,844,292 | 10/1974 | Bolduc | 128/419 P |
| 3,880,169 | 4/1975 | Starr et al. | 128/418 |
| 3,976,082 | 8/1976 | Schmitt | 128/418 |
| 3,978,865 | 9/1976 | Trabucco | 128/418 |
| 4,058,128 | 11/1977 | Frank et al. | 128/418 |
| 4,066,085 | 1/1978 | Hess | 128/418 |

FOREIGN PATENT DOCUMENTS 1575665 6/1969 France ................................. 128/419 P Primary Examiner—William E. Kamm
Attorney, Agent, or Firm—Woodcock, Washburn, Kurtz & Mackiewicz

[57] ABSTRACT

An epicardial lead is disclosed having plural electrode tips adapted for securing to the epicardium while moving the electrode at a small angle with respect to the external surface of the heart. At least 2 electrode tips are provided which are curved downward from the bottom surface of the electrode head and backward toward the proximal end of the electrode, so that they can be hooked into the epicardium while pulling the entire lead in a generally backward direction along the surface of the heart. Anchor means are provided at the forward or distal tip of the electrode head, with means for projecting the anchor out of the bottom surface and forward so as to anchor the electrode head against forward movement thereof. The result is a lead which can be firmly secured to the epicardium by two quick movements while maintaining the lead in close proximity to the heart surface, such that minimum access to the heart surface is required.

17 Claims, 2 Drawing Figures

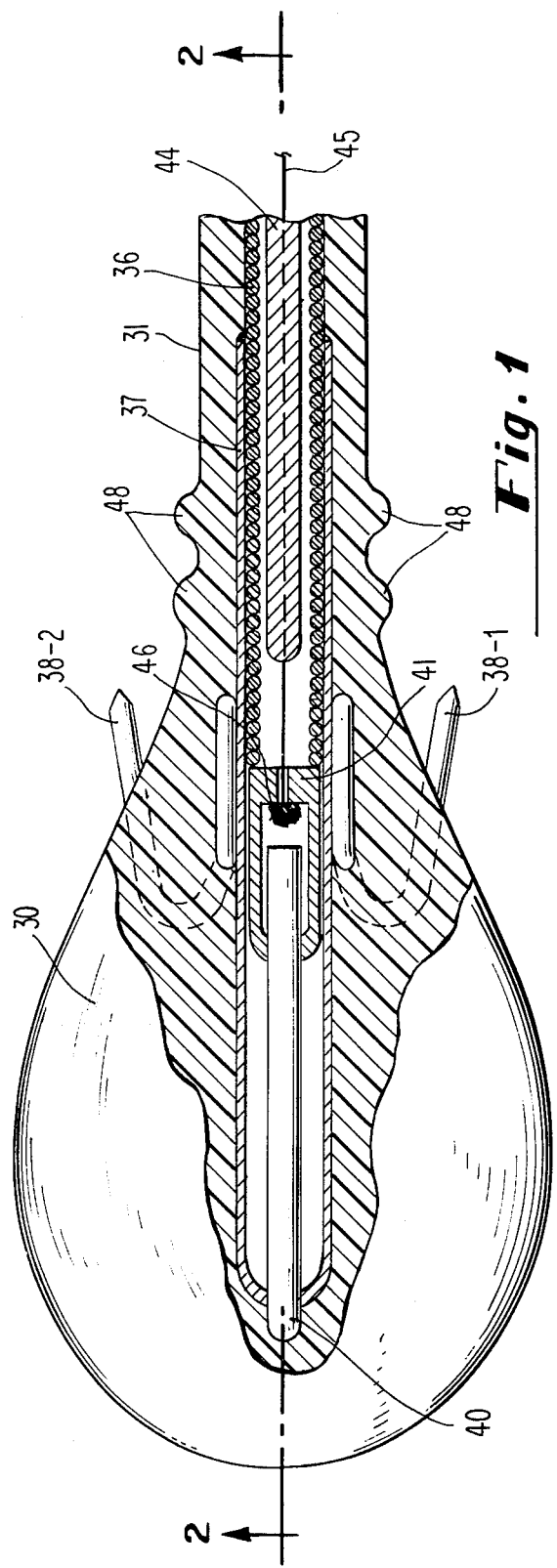
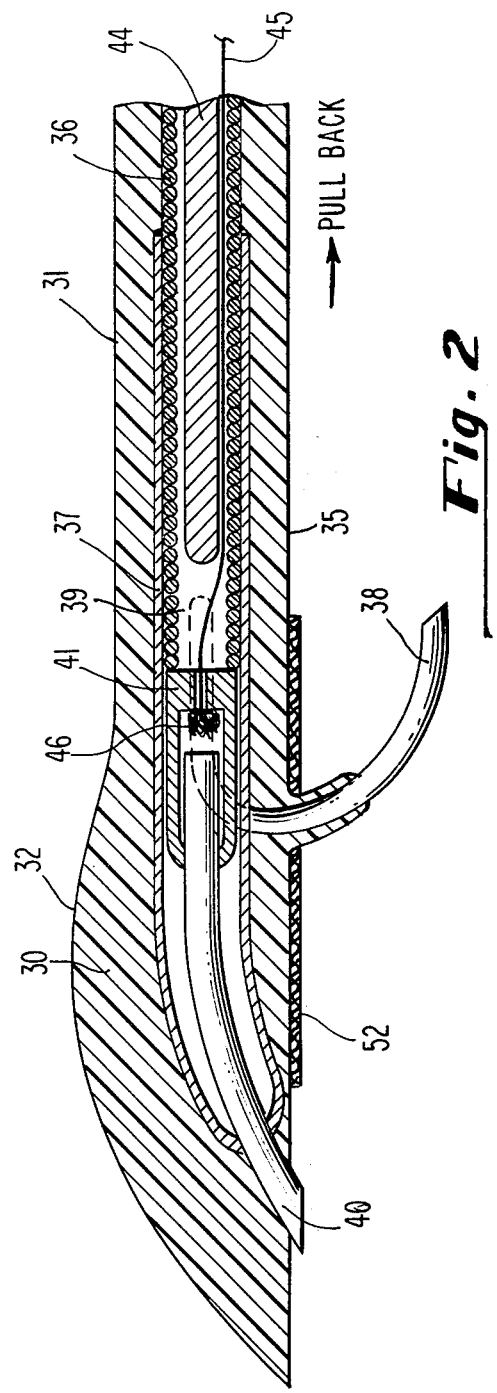

EPICARDIAL LEAD

BACKGROUND OF THE INVENTION

1. Field of the Invention

This invention relates to leads for providing electrical signals to a human organ such as a heart, and, more particularly, to an epicardial lead adapted for quick securing to the heart without the extensive operative procedures heretofore required to suture or connect an epicardial electrode to the outside heart surface.

2. Description of the Prior Art

Heart leads, or catheters, are in widespread use for providing electrical stimulus signals from a pacer device to a patient's heart, for electronic pacing. In a great majority of the cases where pacers are implanted within a patient on a permanent basis, intracardial leads are used wherein the lead is introduced into the heart through a convenient vein. This procedure, of course, avoids the requirement of having direct access to the heart itself, and also avoids the trauma of actually inserting the lead into the heart wall. The closed loop endocardial lead as disclosed in the U.S. Pat. No. 4,026,303, to Babotai, and assigned to the same assignee, has proven very successful for use in a large majority of all cases. However, in a certain percentage of cases it is deemed necessary or desirable to use an external or epicardial lead, wherein the contact tip or tips are mechanically inserted into the epicardium. In this arrangement, it is necessary that the insertion be made with a minimum of trauma but yet be absolutely secure, so that good electrical contact is maintained with the heart wall. Historically, one form of such epicardial lead has involved actually suturing the lead onto the wall, to ensure the required security. However, this has the obvious disadvantage of increasing the complexity of the operative procedure.

In order to overcome the need for this procedure, the industry has developed a so-called screw-in or sutureless lead in the form of a helical coil which is screwed into the heart wall. This lead was developed and discovered by Quinn in U.S. Pat. No. 3,416,534, and further developed as disclosed in the U.S. Pat. No. 3,472,234 to Tachick. However, this type of electrode requires that there be sufficient room to approach the heart wall from a direction more or less normal or perpendicular to the surface, so that the helical coil can be screwed directly into the heart muscle. Even if a normal approach is not required, the physician must have sufficient access to the heart so as to be able to push the electrode tip into the epicardium and rotate it. It has also been found, as seen in the patent to Tachick, that it is necessary to have an accompanying instrument which is used for actual insertion of the electrode into the heart. See also U.S. Pat. Nos. 3,737,579 and 3,875,947, which show further developments in instruments for applying the helical type of screw-in lead. While these leads have enjoyed a reasonable success to date, there remains a need for a simpler type of epicardial lead which reduces the procedures required of the physician who is securing the lead. The need is to find an electrode which increases the simplicity of the procedure, in contrast to recent designs which have increased the complexity of the procedure and have required specific additional instrumentation. There has developed a great need for a simple epicardial lead which can be manually secured by the surgeon with a minimum of procedure and with a minimum of access to the heart wall, and without the need of maintaining implementing devices.

SUMMARY OF THE INVENTION

It is an object of the invention to provide an epicardial lead which permits the securing of such lead to the epicardium of a patient's heart, or to another muscle portion of the patient, which lead is simple to use, provides a highly secure fixation, and does not require an elaborate engaging tool.

It is another object of this invention to provide an epicardial lead which may be attached to a patient's heart without the need for suturing, and which is of a design adapted to be easily and reliably fixed to the patient's heart without requiring the procedures required heretofore to gain sufficient access to the heart to attach sutureless screw-in type leads.

It is a further object of this invention to provide an electrode adapted for quick and secure fixation to a patient's heart, for transmitting stimulating signals to such heart, which lead when fixated is not subject to lateral, vertical or rotational movement.

it is a further object of this invention to provide a lead adapted to be secured to the outside of a patient's heart, for delivering electrical signals thereto, the use of which lead requires a minimum of procedures for gaining access to the patient's heart for attachment of said lead thereto.

It is a further object of this invention to provide a method of attaching a lead to a human heart from the outside of such heart, without requiring rotating of such lead while attaching it.

In accordance with the above objects, there is provided an epicardial lead having electrode contact tip means extending from the bottom thereof and of a form adapted for insertion into the patient's heart while the lead is being pulled back, in combination with an anchor adapted to be inserted forwardly into the patient's heart after prior insertion of the electrode tip means, whereby the lead is secure and invulnerable to movement due to lateral, vertical or rotational movement of the heart wall itself. In the preferred embodiment, at least 2 backward-extending electrode tips are utilized, each tip being pointed at its end for easy insertion into the heart wall, the tips being electrically connected to a conductor which is adapted at the other end of the lead for connection to an electronic device such as a cardiac pacemaker.

BRIEF DESCRIPTION OF THE DRAWINGS

FIG. 1 is a top view partially broken away to show details of the lead of this invention.

FIG. 2 is a sectional view taken along the line 2—2 of FIG. 1, of the head end of the electrode lead of this invention.

DESCRIPTION OF THE PREFERRED EMBODIMENTS

Referring now to FIGS. 1 and 2, there is shown an electrode head which is an extension of lead 31. Lead 31 comprises a length which is typical for use in an application such as providing stimulus signals from a cardiac pacer to a heart, and at its proximal end (not shown) is adapted with conventional terminal means for making electrical contact with the pacer. The length of the lead comprises the standard arrangement of a conductor, or conductors, encased in a suitable insulating cover of a bio-compatible material. The distal end, as shown, comprises a casing 30 suitably made of silicone rubber, which encases the lead head. The lead head has a bottom surface 35 which is generally flat, which surface is adapted to be placed proximate to and in contact with the epicardium, or external heart surface. The electrical signals are transmitted from the pacer by conductor 36, shown diagrammatically as a helical coil. Conductor 36 is placed in firm electrical contact with metallic bushing 37, which bushing defines an interior space designated by the numeral 39. Connected to the outside of bushing 37, on opposite sides thereof, are electrode contact elements 38-1 and 38-2 respectively. The elements 38 are suitably welded to bushing 37, to provide the necessary mechanical and electrical contact. Elements 38 are preferably platinum-iridium wires, with pointed tips at each end, as shown in the illustrative drawings. Although two such tips are shown, it is to be understood that contact tip means 38 may comprise any desired plurality of tip elements. The tip elements 38-1 and 38-2 are extended through the bottom 35 of the lead in water-tight relation, so that no moisture seeps up through the casing 31 into the interior 39.

The geometry of the contact tips is a very important feature from the viewpoint of providing for ease of fixation of the lead to the epicardium. As illustrated, the tips have a component of direction extending normal to the bottom surface 35 at the point where they extend through such bottom surface. However, the tips are curvilinear, and extend with a substantial component which is parallel to the bottom surface 35, and at the point of the tip end as illustrated the contact tips are approximately parallel thereto. As shown in FIG. 1, the tips 38 may also have a small lateral extension away from the longitudinal axis of the lead, which is defined substantially by the axis within coil 36. It is seen that this geometry permits the pointed ends of the tips to be inserted into the epicardium by placing the lead head on or near the surface of the epicardium and pulling the entire lead in a backward direction, toward the proximal end thereof, as indicated by the arrow and the designation "pull back" therewith. Since the height of the lead, as seen in FIG. 2, from the bottom of the tip 38 to the top portion of the head defined by the curvature of the silicone rubber, is very small, on the order of about a cm, it is possible to position the lead for insertion with a minimum of space for access to the epicardium. Indeed, the physician implanting the lead need only be able to slide the lead forward along the surface of the heart to the point where it is desired to insert the contact tips, and then pull back while pressing down slightly so as to position the tips 38 downward and backward into the epicardium. It is seen that this can be done without need for rotating any portion of the lead.

As also seen in FIGS. 1 and 2, there is positioned within the space 39 (defined by bushing 37) a piston 41, which carries an anchor 40 which is normally maintained within the interior of the lead, i.e., within space 39. The piston 41 is of dimensions so that it can slide back and forth through the space 39. The piston is mechanically secured to the proximal end of anchor 40, which anchor has a point at the end thereof and extends through an opening (not shown) in casing 30. The anchor, or forward barb, is preferably constructed of nylon, or other suitable plastic, of sufficient strength so as to provide a good mechanical hook for fixation into the heart. Anchor 40 may also be of a suitable metal. However, it is desirable that the total electrode surface area is about 5-20 mm$^2$, and so the metal anchor may be coated with an insulator such as plastic. The piston, which is preferably metal, is crimped at its distal end around the proximal end of anchor 40, to obtain good permanent mechanical contact. A nylon wire 54 extends through the axial center of lead 31 from the proximal end, where it is free for manipulation by the surgeon. The distal end of nylon wire 45 is threaded through an axial opening in piston 41 to a retaining element 46 which is integral therewith, element 46 being suitably in spherical form, such as a knot, and of diameter such that it cannot be pulled through the opening in the piston. By this means, when the physician pulls back on the nylon wire, the entire piston 41, and also anchor element 40, is withdrawn or pulled into the lead, such that the tip end of the anchor 40 does not extend significantly below surface 35. This is the condition of the lead at the time it is first placed in proximity to the heart, and when the electrode tips 38 are inserted. When tips 38 are securely in place, the physician advances a stylet 44, suitably metallic and of conventional construction, until it abuts the proximal end of piston 41. By pushing forward on stylet 44, the physician causes the piston 41 and anchor 40 to move forward or toward the distal end of the head of the lead, so that the tip of anchor 40 is driven out of the lead and into the epicardium. Note that when this is done the electrode contact tips 38 prevent movement of the electrode head in a back or rearward direction, such that anchor 40 can be extended forward into the epicardium, to provide a good fixation.

Although the preferred embodiment has been shown incorporating only one anchor element 40, anchor 40 could comprise 2 elements or may be forked into 2 ends, so as to provide 4 corner fixation. Indeed, any plurality of elements may be utilized to form the forward anchor. However, it is simplest to have just one forward extending anchor, as shown, and this arrangement provides 3 point fixation, which is sufficient to prevent both lateral and rotational movement of the lead head. As seen in FIG. 1, when electrode contact tips 38-1 and 38-2 are inserted in the heart muscle, and anchor 40 is likewise inserted, there can be no rotational movement of the lead head. Likewise, as is seen from FIG. 2, the curvature of elements 38-1 and 38-2 prevents movement of the electrode head in a direction outward from the surface of the heart. Thus, the lead is entirely secure against movement relative to the heart muscle.

As illustrated in FIG. 2, the distal portion of the lead may comprise a knitted Dacron mesh, as illustrated at 52, which is attached to the bottom surface 35 around the electrode tips 38. Such mesh is good for ensuring ingrowth around contact elements 38, thereby aiding in providing long term mechanical connection. In addition, the neck of the lead, just at the point where it expands to form head 30, may be provided with shoulders 48 configured to provide a convenient position for suturing, if desired by the surgeon. While the design of the electrode lead is such that suturing is not necessary, many surgeons like to have the ability to suture in any event.

It is thus seen that there is disclosed an epicardial lead which is particularly adapted for secure fixation to the exterior of the heart muscle of a patient, or to the exterior of any other type of organ to which it is desired to attach the lead. The geometrical design of the contact tip elements 38 is such that the electrode is quickly secured by positioning it on or at the surface of the epicardium and simply pulling the lead back while pressing it into the heart surface. Following this, the surgeon simply manipulates the stylet 44 forward so as to secure the anchor 40. It is to be noted that there is suitably small enough clearance between the piston 41 and the bushing 37 so that there is a reasonable friction fit therebetween, such that the stylet can easily force the piston forward, but that when the stylet is withdrawn there is no chance that the piston 41 would relax in a proximal or backward direction, bringing the anchor back out. The nylon wire 45 is of suitable tensile strength that it is reliable for pulling the piston 41 backward as desired.

An additional advantage of the lead as presented herein is that 2 contact tips are provided, thereby giving a redundant reliability. If one tip breaks or for some reason does not make good electrical contact with the epicardium, the other tip is still there. It is desirable to limit the total surface of the stimulating tip, and for this reason the total surface provided by the 2 elements 38 is suitably limited to about 5 to 20 mm$^2$. The thickness of the platinum irridium contact elements 38 is suitably 0.6 to 0.7 mm. Depending upon the length of the elements 38, which is a matter of design choice, insulation may suitably be provided to cover a portion of each of the electrode tips, in order to control the effective stimulus surface.

The embodiment disclosed in the drawings is the preferred embodiment. However, other embodiments are within the scope of the invention. For example, the elements 38 and 40 may be interchanged, i.e., elements 38 may extend in a forward direction, while element 40 extends in a rearward direction. In this case, the lead is attached by first pushing the lead head forward so that the elements 38 hook into the epicardium, and then anchor 40 is positioned by pulling back on the piston with a wire such as wire 45. As with the preferred embodiment, the lead head provides hook or anchor elements having respective opposite extensions from the bottom surface. Suitably the extensions have opposite longitudinal components with respect to the axis of the lead. At least one of the elements has a generally curvilinear form so that it can be engaged into the heart muscle by a movement at a small angle to the muscle surface.

Likewise, element 40 may be made the contact element, if desired. Alternately, the lead may be a bipolar lead with any two of the elements 38 and 40 having an exposed conducting surface and being connected to conductors which run the length of the lead.

As used herein, the term "component of extension" means the portion of extension in a given direction. Thus, referring to FIG. 2, element 38 has a component of extension normal to surface 35, as well as a component of extension parallel to surface 35. As seen in FIG. 1, elements 38-1 and 38-2 each have a lateral component of extension away from the longitudinal section line 2—2. The drawings are understood to be illustrative and not exactly to scale, it being noted for example that elements 38 may be extended rearwardly further than shown. They may also have an extension that curves somewhat back up toward the surface 35.

I claim:

1. An epicardial lead adapted for attachment to a heart surface, comprising:

a. an encased conductor portion extending substantially the length of said lead, having a conductive element for transmitting electrical signals between a proximal end and a distal end;

b. an insulated head portion integrally connected to the distal end of said conductor portion, having a bottom surface and at least one conductive contact tip element in electrical connection with said conductive element, said tip element extending downward and backward from said bottom surface, having a longitudinal component of extension in the proximal direction; and c. anchor means having at least one moveable anchor element extending forward and downward from said bottom surface, for engaging said heart surface.

2. The lead as described in claim 1, comprising positioning means for moving said anchor means, whereby said anchor means can be positioned in engagement with said heart surface.

3. The lead as described in claim 2, wherein said positioning means comprises a stylet.

4. The lead as described in claim 2, wherein said positioning means comprises means for withdrawing said anchor means from an engaged position.

5. The lead as described in claim 1, wherein said anchor means comprises a single anchor element having a pointed tip.

6. The lead as described in claim 1, comprising two contact tip elements, each of said contact tip elements having an exposed conductive portion and being in electrical contact with said conductive element, each of said contact tip elements having an extension with a backward component toward the proximal end of said lead.

7. The lead as described in claim 1, wherein said anchor means is located distally from said at least one conductive hook element.

8. A lead adapted for implantation in a human, for direct attachment exteriorly into the wall of a human organ, said lead having an encased portion extending substantially its full length and containing a conductive element for transmitting electrical signals, said lead havig at its distal end a lead head adapted for attachment to said organ wall by approaching said wall from a small angle thereto, characterized by said lead head comprising first engaging means for engaging said organ wall when said first engaging means is moved in a first direction at a small angle to the surface of said body organ; and second engaging means for engaging said organ wall, extending from said lead head with an extension substantially opposite to said first direction.

9. The lead as described in claim 8, wherein said first engaging means is adapted to engage said organ as said electrode tip is moved in a proximal direction, and said second engaging means is adapted to be extended in a distal direction.

10. The lead as described in claim 8, wherein said first engaging means comprises an exposed conductive tip which is electrically connected to said conductive element.

11. The lead as described in claim 10, wherein said second engaging means is moveable and comprising positioning means for moving said second engaging means into and out of engagement with said organ wall.

12. The lead as described in claim 8, wherein at least one of said engaging means comprises an exposed conductive tip and is electrically connected to said conductive element.

13. A lead adapted for direct attachment to a wall of a human organ, said lead being adapted to conduct electrical signals between said organ and a location remote from said organ, said lead having an attachment portion adapted for attachment to said organ and comprising:
  a. a first engaging element having a fixed extension from said portion, said fixed extension having a lateral component and a longitudinal component in a first longitudinal direction; and
  b. a second moveable engaging element adapted to extend from said portion with a longitudinal component of extension in an opposite direction from said first longitudinal direction.

14. The lead as described in claim 13, wherein said first engaging element is curvilinear so that when it is inserted into a surface of said organ and in engaging relation with said organ it provides resistance to movement of said attachment portion normal to said surface.

15. A method of securing an electrode lead exteriorly to the epicardium of a human patient's heart, said lead having a head with first proximal engaging means extending downward from the bottom surface thereof and backward toward the proximal end of said lead, and second engaging means positioned distal of said first engaging means and extendable downward from said bottom surface and forward away from said proximal end, the method comprising positioning the electrode in proximity to the heart surface by advancing the lead forward at a small angle to the heart surface; withdrawing said lead backward and inserting said first engaging means into said heart; and maintaining said first engaging means in said heart and extending said second engaging means forward into said heart.

16. The method as described in claim 15, wherein said second engaging means is extended by inserting a stylet through said lead and causing same to push against said second extending means.

17. A lead adapted for direct attachment to a wall of a human organ, said lead having means for conducting electrical signals between said organ and a remote location, said lead having an attachment portion with a contacting surface and adapted for attachment to said organ, wherein the improvement consists of:
  a. a pair of first engaging elements extending from said surface, each having a respective fixed curvilinear extension from said surface, each having an extension downward from said surface, a lateral extension, and a longitudinal extension, said lateral extensions being opposite and said longitudinal extensions being in a first common longitudinal direction; and
  b. a moveable engaging element adapted to extend from said surface, having a longitudinal extension in a second direction opposite to said first direction.

* * * * *